United States Patent [19]

Scheps

[11] Patent Number: 4,942,029
[45] Date of Patent: Jul. 17, 1990

[54] MEDICATED SKIN PREPARATION

[75] Inventor: Milton H. Scheps, Largo, Fla.

[73] Assignee: Smith & Nephew United, Inc., Largo, Fla.

[21] Appl. No.: 323,625

[22] Filed: Mar. 14, 1989

Related U.S. Application Data

[63] Continuation of Ser. No. 909,141, Sep. 19, 1986, abandoned.

[51] Int. Cl.$^5$ ............................................. A61K 31/74
[52] U.S. Cl. ...................................................... 424/78
[58] Field of Search ........................................... 424/78

[56] References Cited

U.S. PATENT DOCUMENTS 4,007,263  2/1977  Pichierri ................................ 424/78
4,294,852  10/1981  Wildnauer et al. ............. 514/721 X Primary Examiner—Leonard Schenkman
Attorney, Agent, or Firm—Jacobs & Jacobs

[57] ABSTRACT

A medicated skin composition comprises a mixture of a copolymer of methylvinylether and methacrylic acid, isopropyl alcohol, citric acid ester plasticizer and 2,4,4'-trichloro-2'-hydroxydiphenyl ether. This composition is applied to the skin to form an antimicrobial barrier.

17 Claims, No Drawings

MEDICATED SKIN PREPARATION

This is a continuation of Ser. No. 909,141 filed September 19, 1986 now abandoned.

BACKGROUND OF THE INVENTION

This invention relates to a medicated skin composition and a process for forming an antimicrobial barrier on skin by applying said medicated skin composition to the skin.

Medicated skin compositions are known and are currently on the market. One commercial product at the moment is Sween Prep (trade mark) which comprises chloroxylenol as a bacteriostat. Although some antimicrobial activity is attained with such commercial products, the duration of activity has been limited.

SUMMARY OF THE INVENTION

The medicated skin composition having extended antimicrobial activity according to the invention comprises a film-forming amount of a copolymer of methylvinylether and methacrylic acid, isopropyl alcohol solvent, a plasticizing amount of citric acid ester plasticizer and an antimicrobially effective amount of 2,4,4'-trichloro-2'-hydroxydiphenyl ether.

Said composition is applied to the skin to form an antimicrobial barrier on the skin.

The film-forming copolymer of methylvinylether and maleic acid is present in the composition in sufficient amount to form a film on the skin on application to the skin. Such amount generally ranges from about 10 to 20% by weight of the total composition. The copolymer is usually present in the form of its $C_1-C_6$-alkyl ester, e.g. the butyl ester. A useful product is Gantrez ® ES-435 of GAF Corporation which is the butyl monoester of poly(methyl vinyl ether and maleic acid).

The isopropyl alcohol is present in an amount sufficient to dissolve the other ingredients of the composition. Generally, the alcohol solvent will be present in an amount ranging from about 80 to 90% by weight of the total composition.

The citric acid ester plasticizer is present in a plasticizing amount generally ranging from about 0.1 to 3% by weight of the total composition. Examples of suitable citric acid ester plasticizers are trialkyl esters of citric acid wherein each alkyl has from 1 to 6 carbon atoms. A preferred citric acid ester is acetyl tributyl citrate, which is available as Citroflex ® A-4.

The antimicrobial compound 2,4,4'-trichloro-2'-hydroxydiphenyl ether (Triclosan) is present in an amount effective for antimicrobial activity of the skin composition, generally in an amount from 0.1 to 2% by weight of the total composition.

DETAILED DESCRIPTION OF THE INVENTION

The skin composition of the invention is prepared by thorough mixing of the ingredients according to procedures standard in the preparation of medicated skin compositions. Tanks, homogenizer and other manufacturing equipment coming into contact with the ingredients of the skin composition are generally washed with hot detergent solution, rinsed, sanitized with an antiseptic such as a chlorine solution and again rinsed before use.

The skin composition may be made in different forms, e.g. as a brush-on liquid, an aerosol spray, a medicated skin wipe or a swab.

The brush-on liquid is generally prepared by slowly adding 2,4,4'-trichloro-2'-hydroxydiphenyl ether to isopropylalcohol solvent, and thorough mixing until dissolution of the ether in the solvent. The citric acid ester plasticizer and the copolymer of methylvinylether and maleic acid are then added and mixed until dissolution and formation of a homogeneous solution.

The aerosol spray is generally prepared by mixing the medicated skin composition of the invertion with a conventional propellant such as hydrocarbons, e.g. propane or butane, and fluorinated hydrocarbons. Commonly, equal weight amounts of the medicated skin composition and the propellant are used.

The medicated skin wipe may be prepared by impregnating a paper web material with a homogeneous solution such as described above for use as a brush-on liquid. The medicated skin wipe is packaged in an air-tight enclosure to avoid unsanitary conditions before use. The package material is conveniently a three ply foil laminate consisting of a paper layer, a polypropylene layer and a layer of Surlyn ®, which is a thermoplastic polymer.

The following examples illustrate the invention.

EXAMPLE 1

The following ingredients are combined in the percentage by weight indicated:

MEDICATED SKIN PREPARATION

| Acetyl tributyl citrate | 0.42% b.w. |
| --- | --- |
| Triclosan | 0.25% b.w |
| Gantrez ES-435 | 14.00% b.w |
| Isopropyl alcohol | 85.33% b.w. |

Isopropyl alcohol is added to a presanitized, stainless steel vessel equipped with turbine agitation. Triclosan is slowly added and mixed well until complete dissolution. The acetyl tributyl citrate and Gantrez ES-435 are added and mixed thoroughly for complete dissolution and obtaining a homogeneous solution.

EXAMPLE 2

AEROSOL

The following ingredients are combined in the percentage by weight indicated:

| Medicated Skin Preparation of Example 1 except for isopropyl alcohol | 24.0% b.w. |
| --- | --- |
| Isopropyl alcohol (99%) | 26.0% b.w |
| Propellant A-46[1] | 50.0% b.w. |

[1]Mixture of propane and butane under a pressure of 46 pounds at 70° F.

The medicated skin preparation and the isopropyl alcohol are mixed with a high speed mixer for 15 minutes. The mixture is filled into aerosol cans with an aerosol filling machine. The propellant is added to each can with the filling machine. Each can contains 4⅜ oz. wt. of product of which 2⅜ oz. wt. is the medicated skin preparation and 2⅜ oz. wt. is the propellant.

I claim:

1. A medicated skin composition useful for application to human skin to form an antimicrobial barrier on the skin which composition comprises a film forming amount of a copolymer of methylvinylether and maleic acid, an effective amount of a citric acid ester plasticizer for the copolymer, an antimicrobially effective amount of 2,4,4'-trichloro-2'-hydroxydiphenyl ether and a alcohol solvent therefor.

2. A composition according to claim 1 wherein the copolymer is present in an amount from about 10% to about 20% by weight of the total composition.

3. A composition according to claim 1 wherein the copolymer is in the form of its alkyl ester of 1 to 6 carbon atoms.

4. A composition according to claim 1 wherein the ester is the butyl ester.

5. A composition according to claim 1 wherein the solvent is present in an amount sufficient to dissolve the other ingredients of the composition.

6. A composition according to claim 1 wherein the alcohol solvent is present in an amount of from about 80% to about 90% by weight of the total composition.

7. A composition according to claim 1 wherein the solvent is isopropyl alcohol.

8. A composition according to claim 1 wherein the plasticizer is present in an amount from about 0.1 to about 3% by weight of the total composition.

9. A composition according to claim 1 wherein the plasticizer is a citric acid ester.

10. A composition according to claim 1 wherein the citric acid ester is a trialkyl ester of citric acid wherein each alkyl moiety is of 1 to 6 carbon atoms.

11. A composition according to claim 1 wherein the citric acid ester is acetyl tributyl citrate.

12. A composition according to claim 1 wherein the 2,4,4'-trichloro-2'-hydroxydiphenyl ether is present in an amount from about 0.1% to about 2% by weight of the total composition.

13. A composition according to claim 1 in the form of a brush-on liquid.

14. A composition according to claim 1 in the form of an aerosol spray.

15. A composition according to claim 1 in the form of a medicated skin wipe.

16. A composition according to claim 1 in the form of a swab.

17. A method of applying an antimicrobial barrier to human skin which comprises applying to a human skin in need thereof an effective amount of a composition according to claim 1.

* * * * *